US006923967B1

(12) United States Patent
Lignell

(10) Patent No.: US 6,923,967 B1
(45) Date of Patent: Aug. 2, 2005

(54) TREATMENT OF DYSPEPSIA

(75) Inventor: Ake Lignell, Varmdo (SE)

(73) Assignee: Astacarotene AB, Gustavsberg (SE)

( * ) Notice: Subject to any disclaimer, the term of this patent is extended or adjusted under 35 U.S.C. 154(b) by 0 days.

(21) Appl. No.: 09/463,958

(22) PCT Filed: Oct. 8, 1999

(86) PCT No.: PCT/EP99/07551

§ 371 (c)(1),
(2), (4) Date: Jan. 17, 2002

(87) PCT Pub. No.: WO00/23064

PCT Pub. Date: Apr. 27, 2000

(30) Foreign Application Priority Data

Oct. 16, 1998 (SE) .................................... 9803541

(51) Int. Cl.$^7$ ........................................... A61K 35/78
(52) U.S. Cl. ................................................. 424/195.17
(58) Field of Search .................................. 424/195.17

(56) References Cited

U.S. PATENT DOCUMENTS 5,229,418 A * 7/1993 Collington et al.

FOREIGN PATENT DOCUMENTS

| EP | 0770385 A | | 2/1997 |
|---|---|---|---|
| JP | 57-105145 A | * | 6/1982 |
| WO | WO 9500130 A | | 5/1996 |
| WO | WO 9623489 A | | 8/1996 |
| WO | WO 9837874 A | | 3/1998 |

OTHER PUBLICATIONS

STN International, File BIOSIS, BIOSIS accession no, 1993:537623, Mozsik, G. et al., "Retinoids as scavengers and gastric cytoprotection in animals, human beings and patients with peptic ulcer," Oxygen free radicals and scavengers in the natural sciences, 1993.

* cited by examiner

Primary Examiner—Susan D. Coe
(74) Attorney, Agent, or Firm—Bacon & Thomas

(57) ABSTRACT

Use of a at least one type of xanthophylls for the preparation of a medicament for prophylactic and/or therapeutic treatment of dyspepsia, is disclosed. The xanthophyll is preferably astaxanthin, e.g. astaxanthin is in a form esterified with fatty acids, such as in algal meal prepared from a culture of the alga *Haematococcus* sp. The medicament may further comprise carbohydrate structures and/or (a) different antioxidant(s). Further, a method of prophylactic and/or therapeutic treatment of dyspepsia in an individual, is described. The method comprises administration to said individual of an dyspepsia-alleviating amount of a medicament comprising at least one type of xanthophylls.

9 Claims, No Drawings

TREATMENT OF DYSPEPSIA

The present invention relates to treatment of dyspepsia. The invention is particularly concerned with the use of at least one type of xanthophylls for the preparation of a medicament for prophylactic and/or therapeutic treatment of dyspepsia, and a method of treating dyspepsia. A preferred xanthophyll is astaxanthin.

BACKGROUND OF THE INVENTION

Dyspepsia, or indigestion, is one of the most common gastrointestinal disorders or diseases in both animals and humans. Dyspepsia is persistent or recurrent abdominal pain or abdominal discomfort centered in the upper abdomen. Dyspepsia refers to symptoms in the upper abdomen that are considered to be related to the upper alimentary tract. Often dyspepsia is temporary and disappears spontaneously. In case alleviation of the symptoms is desired, ingestion of antacids is often the first choice of treatment. Antacids are normally not taken prophylactically.

However, there are several alternative therapeutic treatments of dyspepsia, and the present invention provides a new alternative, which may also be used for prophylactic treatment.

DESCRIPTION OF THE INVENTION

The present invention is directed to the use of at least one type of xanthophylls for the preparation of a medicament for prophylactic and/or therapeutic treatment of dyspepsia.

In a preferred embodiment the xanthophyll is astaxanthin, especially astaxanthin in a form esterified with fatty acids. The astaxanthin in esterified form is suitably provided in the form of algal meal prepared from a culture of the alga *Haematococcus* sp.

The medicament may further comprise carbohydrate structures, such as lipopolysaccharides, polysaccharides and glycoproteins, and/or one or several different antioxidant(s), such as ascorbic acid (vitamin C) and tocopherol (vitamin E).

The medicament is preferably in the form of unit doses adapted for a daily dosage of xanthophyll(s) in the range of 0.05 to 1 mg per kg body weight of an individual, which is an animal or a human.

The invention is also directed to a method of prophylactic and/or therapeutic treatment of dyspepsia in an individual, which comprises administration to said individual of an dyspepsia-alleviating amount of a medicament comprising at least one type of xanthophylls.

In a preferred embodiment the xanthophyll is astaxanthin, especially astaxanthin in a form esterified with fatty acids. The astaxanthin in esterified form is suitably provided in the form of algal meal prepared from a culture of the alga *Haematococcus* sp.

The medicament may further comprise carbohydrate structures, such as lipopolysaccharides, polysaccharides and glycoproteins, and/or one or several different antioxidant(s), such as ascorbic acid (vitamin C) and tocopherol (vitamin E).

Preferably, the dyspepsia-alleviating amount of the medicament comprises xanthophyll(s) in the range of 0.05 to 1 mg per kg body weight of the individual, which is an animal or a human.

The at least one type of xanthophylls that are used in the present invention may comprise a mixture of different types of xanthophylls or different forms of the same xanthophyll, such as a mixture of synthetic astaxanthin and naturally produced astaxanthin.

The mechanism of the prophylactic and therapeutic effect of the xanthophylles in the treatment of dyspepsia is not known, but it should be noted that they possess strong antioxidative properties and that they are soluble in fats and oils.

At present, the most preferred embodiment of the invention comprises algal meal having astaxanthin in esterified form with fatty acids dissolved in small droplets of naturally occurring oil and naturally occurring carbohydrate structures in the partially disrupted cell walls.

The medicament used in the invention may comprise additional ingredients which are pharmacologically acceptable inactive or active in prophylactic and/or therapeutic use, such as flavoring agents.

The medicament may be presented in a separate unit dose or in mixture with food. Examples of separate unit doses are tablets, gelatin capsules and predetermined amounts of solutions, e.g. oil solutions, or emulsions, e.g. water-in-oil or oil-in-water emulsions. Examples of foods in which the preparation of the invention may be incorporated is dairy products, such as yoghurt, chocolate and cereals.

Experiments

The experiments were conducted on 15 human volunteers experiencing symptoms of dyspepsia that did not disappear spontaneously. They were given 2 to 10 capsules per day containing algal meal produced by culturing of the algae *Haematococcus* sp. by AstaCarotene AB, Gustavsberg, Sweden. (These capsules are sold as an anti-oxidant and they contain 4 mg astaxanthin per capsule, with the instruction to take one capsule per day.)

This double to ten times the recommended dose, i.e. 8–40 mg astaxanthin per day, eliminated or drastically alleviated the symptoms of dyspepsia in all volunteers in 1–3 weeks, and no side effects were reported.

Astaxanthin from other sources, and other xanthophylls as well, are expected to be similarly useful for the purposes of the invention. An advantage of using astaxanthin from algae is, however, that the astaxanthin exists in a form esterified with fatty acids [Renström B. et al, 1981, Phytochem 20(11):2561–2564], which esterified astaxanthin thereby is more stable during handling and storage than free astaxanthin.

What is claimed is:

1. A method for alleviating symptoms of indigestion in a human, which comprises administering an indigestion alleviating effective amount of a medicament to said human wherein said medicament consists essentially of at least one type of xanthophyll as an active ingredient.

2. The method according to claim 1, wherein the xanthophyll is astaxanthin.

3. The method according to claim 2, wherein the astaxanthin is in a form esterified with fatty acids.

4. The method according to claim 3, wherein the astaxanthin in esterified form is provided in the form of algal meal prepared from a culture of the alga *Haematococcus* sp.

5. The method according claim 1, wherein the medicament consists essentially of said at least one type of xanthophyll and at least one carbohydrate.

6. The method according to claim 1, wherein the medicament consists essentially of said at least one type of xanthophyll and a different antioxidant.

7. The method according to claim 1, wherein said xanthophyll is administered in the range of 0.05 to 1 mg per kg body weight of the human.

8. The method according to claim 1, wherein the medicament consists essentially of said at least one type of xanthophyll and different antioxidants.

9. The method according to claim 7, wherein more than one type of xanthophyll is administered to said human.

* * * * *